United States Patent
Beckers et al.

(10) Patent No.: US 8,304,564 B2
(45) Date of Patent: Nov. 6, 2012

(54) PROCESS FOR THE REMOVING POLY(PROPYLENE OXIDE) FROM PROPYLENE OXIDE BY MEMBRANE SEPARATION

(75) Inventors: Johannes Gerhardus Joseph Beckers, Amsterdam (NL); Johannes Leendert Willem Cornelis Den Boestert, Amsterdam (NL); Nigel Wagstaff, Amsterdam (NL)

(73) Assignee: Shell Oil Company, Houston, TX (US)

( * ) Notice: Subject to any disclaimer, the term of this patent is extended or adjusted under 35 U.S.C. 154(b) by 541 days.

(21) Appl. No.: 12/519,992

(22) PCT Filed: Dec. 18, 2007

(86) PCT No.: PCT/EP2007/064113
§ 371 (c)(1),
(2), (4) Date: Dec. 3, 2009

(87) PCT Pub. No.: WO2008/074791
PCT Pub. Date: Jun. 26, 2008

(65) Prior Publication Data
US 2010/0105959 A1    Apr. 29, 2010

(30) Foreign Application Priority Data
Dec. 20, 2006   (EP) .................................... 06126675

(51) Int. Cl.
*C07D 301/32*   (2006.01)
*C08K 5/00*   (2006.01)
(52) U.S. Cl. ........................ 549/541; 524/291
(58) Field of Classification Search .................. 521/174; 525/438; 549/542, 541; 524/291
See application file for complete search history.

(56) References Cited

U.S. PATENT DOCUMENTS

| | | | |
|---|---|---|---|
| 4,507,475 A | 3/1985 | Straehle et al. | 536/120 |
| 4,692,535 A | 9/1987 | Larson et al. | 549/542 |
| 4,879,396 A | 11/1989 | Ozero | 549/534 |
| 4,904,807 A | 2/1990 | Ozero | 549/534 |
| 4,946,939 A | 8/1990 | Murphy et al. | 528/421 |
| 5,069,686 A | 12/1991 | Baker et al. | 55/16 |
| 5,093,002 A | 3/1992 | Pasternak | 210/500.27 |
| 5,102,551 A | 4/1992 | Pasternak | 210/651 |
| 5,150,118 A | 9/1992 | Finkle et al. | 341/23 |
| 5,198,117 A | 3/1993 | Grierson et al. | 210/638 |

(Continued)

FOREIGN PATENT DOCUMENTS
CA   2206626   11/1998

(Continued)

OTHER PUBLICATIONS

Polyurethane Handbook/Chemistry—Raw Materials—Processing—Application—Properties by Günter Oertel, Carl Hanser Verlag, Munich 1985, p. 201.

(Continued)

*Primary Examiner* — Taylor Victor Oh

(57) ABSTRACT

The invention relates to a process for removing poly(propylene oxide) from propylene oxide by membrane separation, wherein a membrane having an average pore size of from 0 to 5 nm is used. In said process, a liquid feed comprising propylene oxide and poly(propylene oxide) may be separated by the membrane into a permeate comprising propylene oxide and either no poly(propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

10 Claims, 1 Drawing Sheet

U.S. PATENT DOCUMENTS

| | | | |
|---|---|---|---|
| 5,248,794 A | 9/1993 | Chappell et al. | 549/541 |
| 5,254,227 A | 10/1993 | Cawlfield et al. | 204/131 |
| 5,275,726 A | 1/1994 | Feimer et al. | 210/321.74 |
| 5,350,521 A | 9/1994 | Andriollo et al. | 210/653 |
| 5,440,058 A | 8/1995 | Hoffman et al. | 549/538 |
| 5,458,774 A | 10/1995 | Mannapperuma | 210/321.83 |
| 5,698,011 A | 12/1997 | Chung et al. | 95/45 |
| 2002/0017490 A1* | 2/2002 | Cossee et al. | 210/651 |
| 2003/0211935 A1 | 11/2003 | Le-Khac | 502/162 |
| 2006/0106237 A1 | 5/2006 | Miller | 549/532 |

FOREIGN PATENT DOCUMENTS

| | | |
|---|---|---|
| CN | 1117490 | 2/1996 |
| DE | 10155470 | 5/2003 |
| EP | 0181621 | 5/1986 |
| EP | 0524816 | 1/1993 |
| EP | 0703936 | 4/1999 |
| EP | 1357103 | 10/2003 |
| GB | 2348200 | 9/2000 |
| WO | WO9627430 | 9/1996 |
| WO | WO9927036 | 6/1999 |
| WO | WO9938825 | 8/1999 |
| WO | WO0055148 | 9/2000 |
| WO | WO0160771 | 8/2001 |
| WO | WO0242356 | 5/2002 |
| WO | WO03035803 | 5/2003 |
| WO | WO2004092308 | 10/2004 |
| WO | WO2005042672 | 5/2005 |
| WO | WO2006040307 | 4/2006 |
| WO | WO2006040328 | 4/2006 |

OTHER PUBLICATIONS

Encyclopedia of Chemical Engineering, $4^{th}$ Ed. 1995, John Wiley & Sons Inc., vol. 16, pp. 158-164.

Robinson et al., "The influence of Crosslinking on the Separation Performance of PDMS Nanofiltration Membranes," Inc. Eng. Chem. Res. 44, pp. 3238-3248, 2005.

Tarleton et al., "Non-aqueous nanofiltration: solute rejection in non-polar binary systems," Journal of Membrane Science, 2005, vol. 252, pp. 123-131.

Robinson et al., "Solvent flux through dense polymeric nanofiltration membranes," Journal of Membrane Science, 2004, vol. 230, pp. 29-37.

"Basic Principles of Membrane Technology," Marcel Mulder, second edition, Kluwer Academic Publishers, 1996.

* cited by examiner

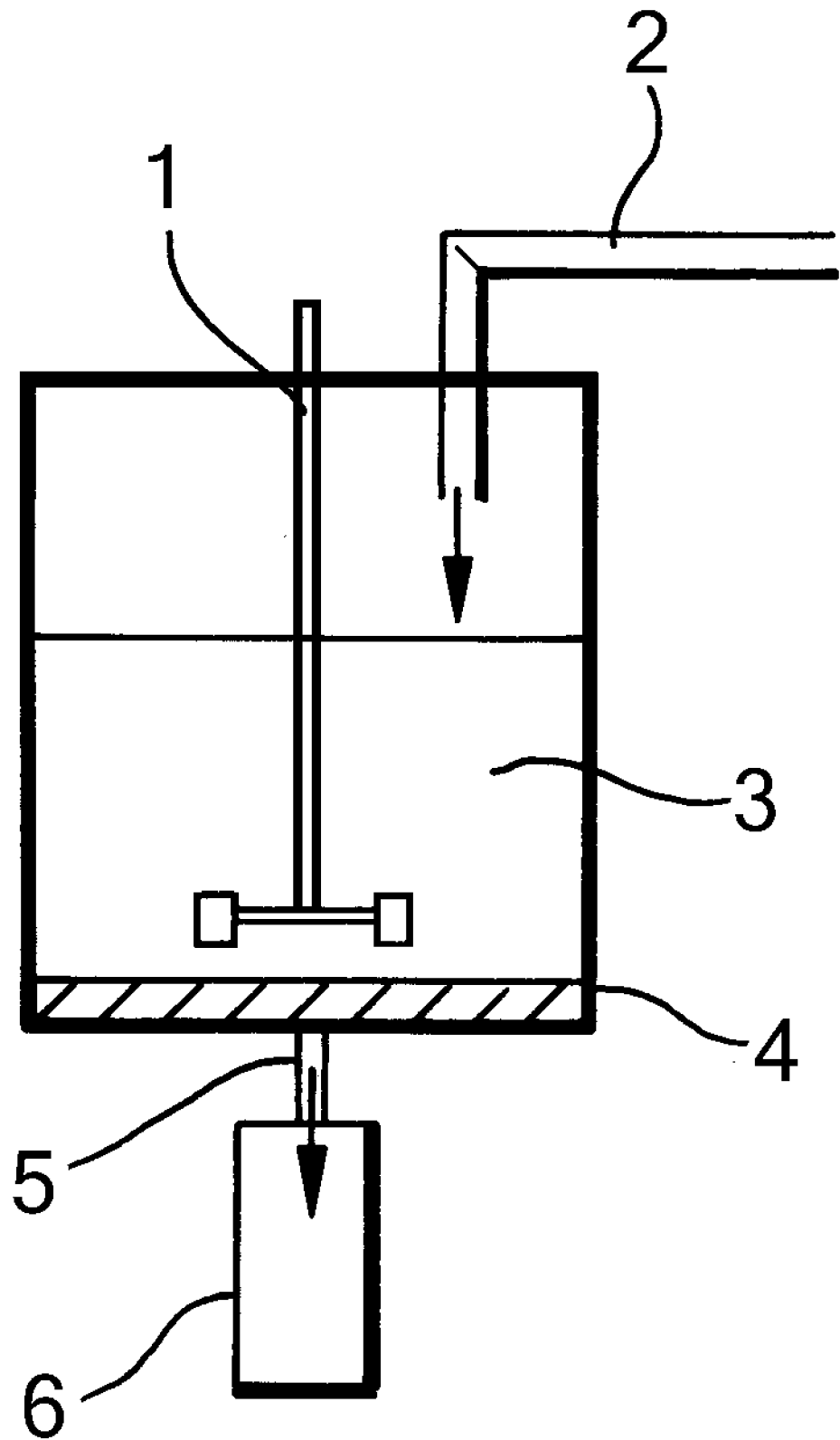

US 8,304,564 B2

PROCESS FOR THE REMOVING POLY(PROPYLENE OXIDE) FROM PROPYLENE OXIDE BY MEMBRANE SEPARATION

The present application claims priority from European Patent Application 06126675.5 filed 20 Dec. 2006.

FIELD OF THE INVENTION

The present invention relates to a process for removing poly(propylene oxide) from propylene oxide by membrane separation.

BACKGROUND OF THE INVENTION

Propylene oxide is widely used as precursor for preparing polyether polyols, which upon reaction with polyisocyanate compounds yield polyurethanes. Typically, methods for preparing polyether polyols involve reacting a starting compound having a plurality of active hydrogen atoms with propylene oxide, optionally together with one or more other alkylene oxides like ethylene oxide or butylene oxide. Suitable starting compounds include polyfunctional alcohols, generally containing 2 to 6 hydroxyl groups. Examples of such alcohols are glycols, glycerol, pentaerythritol, trimethylolpropane, triethanolamine, sorbitol, mannitol, etc. Usually a strong base like potassium hydroxide is used as a catalyst in this type of reaction.

The quality of the propylene oxide used to prepare the polyether polyol has significant impact on the quality of the polyurethane foams eventually obtained, especially when these foams are high resilience flexible polyurethane foams. Particularly the presence of poly(propylene oxide) is known to cause undesired effects in the polyurethane foam formation. Examples of such undesired effects are the occurrence of blow holes, low foam rise and even collapse of the foam formed. Particularly, in moulding applications, the presence of poly(propylene oxide) in the propylene oxide used for preparing the starting polyether polyol may cause problems in terms of quality of the polyurethane foam. The presence of poly(propylene oxide) in propylene oxide used for preparing a polyether polyol for making slabstock polyurethane foams, may be less problematic.

In producing slabstock polyurethane foams, slabs of polyurethane foam are produced continuously or discontinuously as semi-finished products and are finally cut to the required size and shape. The characteristic feature of moulded polyurethane foams in which they fundamentally differ from slabstock polyurethane foams, is the manner of their production. This proceeds by reaction of the polyurethane raw materials in moulds. The finished moulded product no longer has to be cut to the required size and shape. For a further description of the differences between slabstock and moulded polyurethane foams, reference is made to handbooks on polyurethane foams, such as "Polyurethane Handbook/Chemistry—Raw Materials—Processing—Application—Properties" by Günter Oertel (Carl Hanser Verlag, Munich 1985).

It has appeared in practice that, in general, where propylene oxide is to be used to prepare a polyether polyol for making moulded polyurethane foams, no more than 1 ppm of poly (propylene oxide) should be present in said propylene oxide. If more propylene oxide is present, one or more of the above-mentioned undesired effects may occur when making the foam. On the other hand, where propylene oxide is to be used to prepare a polyether polyol for making slabstock polyurethane foams, in general, up to 3 ppm of poly(propylene oxide) may be present in the propylene oxide.

Methods for manufacturing propylene oxide are well known in the art. Commercial production normally takes place via the chlorohydrin process or via the hydroperoxide process. In the latter process propene is reacted with an organic hydroperoxide. This hydroperoxide is either tert-butyl hydroperoxide or ethylbenzene hydroperoxide. In the first case tert-butyl alcohol is formed as a co-product (to be further converted into methyl tert-butyl ether), in the second case styrene is formed as the co-product. In the chlorohydrin process chlorine, propene and water are reacted to form propylene chlorohydrin, which is subsequently dehydrochlorinated with calcium hydroxide to form propylene oxide. For the purpose of the purification of propylene oxide it is immaterial which preparation route is used. Namely, in all processes poly(propylene oxide) is formed in undesirably high quantities. Moreover, it is known (e.g. from U.S. Pat. No. 4,692,535) that high molecular weight poly(propylene oxide) may be formed during storage or transport, for example upon contact with a metal and/or metal oxide, such as metal oxide of carbon steel.

One method for purification of propylene oxide by membrane separation is known from U.S. Pat. No. 5,248,794. According to this method, suitable membranes are poly(vinylidene fluoride) and poly(acrylonitrile) polymeric membranes. Such polymers are commonly used in the art as materials for ultrafiltration membranes. See for example Table II.12 at page 56 of "Basic Principles of Membrane Technology", Marcel Mulder, second edition, Kluwer Academic Publishers, 1996. In said Table II.12, poly(vinylidene fluoride) and poly(acrylonitrile), but also polysulfone and cellulose esters, are mentioned as examples of polymers for ultrafiltration membranes. Therefore, the membranes disclosed in U.S. Pat. No. 5,248,794 are ultrafiltration membranes. Ultrafiltration membranes are porous membranes which have an average pore size greater than 5 nm.

In Table 2 of Example 1 of U.S. Pat. No. 5,248,794, poly (propylene oxide) separation results are mentioned for some different types of membranes. The poly(propylene) membranes were not considered suitable. Only the poly(vinylidene fluoride) and poly(acrylonitrile) ultrafiltration membranes were considered suitable for the purpose of U.S. Pat. No. 5,248,794. One way of determining the suitability of a membrane for separating poly(propylene oxide) (PPO) from propylene oxide, is by calculating the PPO rejection, as follows:

$$\text{PPO rejection (\%)} = (1 - ([PPO]_p / [PPO]_f)) \times 100$$

wherein $[PPO]_p$ is the poly(propylene oxide) concentration in the permeate and $[PPO]_f$ is the poly(propylene oxide) concentration in the feed. Where in the present specification reference is made to PPO rejection, the PPO rejection defined in the above way is meant.

In Example 1 of U.S. Pat. No. 5,248,794, using poly(propylene) membranes resulted in a negative PPO rejection. Further, using poly(vinylidene fluoride) and poly(acrylonitrile) ultrafiltration membranes resulted in relatively low PPO rejections (<30%). The poly(propylene oxide) concentrations in the permeates as mentioned in Table 2 of U.S. Pat. No. 5,248,794, are so high that these permeates cannot be used in the production of moulded polyurethane foams and neither in the production of slabstock polyurethane foams.

Further, in Example 2 of U.S. Pat. No. 5,248,794, the same poly(acrylonitrile) membrane as used in Example 1, was tested with a continuous flow of unfiltered propylene oxide over a period of 86 days. The results are listed in Table 3 of U.S. Pat. No. 5,248,794. From this it appears that in the course of time, the PPO rejection increases from a value of only 31% (on day 1) to a maximum of 100% (on days 52 and 55) and then decreases again to a value of only 67% (on day 86). Therefore, the membrane used is disadvantageous in that there is a relatively long waiting period (of about 52 days) before permeate is produced of which the quality is such that it can be used in the production of moulded polyurethane foams and slabstock polyurethane foams. Further, after day 55, permeate of inferior quality is produced again. Besides a low and unstable PPO rejection in time, another disadvantage is that the permeate flow is also unstable. In said Example 2, the permeate flow goes from a maximum value of 90 ml/min. at the beginning of the experiment, to a value of only 37 ml/min. at the end. This indicates that the membrane, being a porous poly(acrylonitrile) ultrafiltration membrane, gets clogged or plugged in the course of time.

In summary, both the selectivity of and the flow (flux) through the membrane used in Example 2 of U.S. Pat. No. 5,248,794 are relatively low and unstable in time. The volume or mass "flux" (volume or mass "permeation rate") is defined as the volume or mass flowing through the membrane per unit area and time (expressed in $l/h/m^2$ and $kg/h/m^2$, respectively). The permeability of a membrane is defined as the flux through the membrane per unit pressure, and is expressed in $l/h/m^2/bar$ or $kg/h/m^2/bar$. When performing the process of U.S. Pat. No. 5,248,794, a strong fluctuation of separation results in time is obtained. This is disadvantageous in that it is difficult to predict whether or not a certain specification, for example a maximum poly(propylene oxide) concentration in PO permeate, can be met on a certain day.

A further method for improving the quality of propylene oxide by membrane separation is known from GB-A-2348200. In this method, liquid propylene oxide is subjected to a treatment using a ceramic ultrafiltration (porous) membrane under such conditions that the amount of poly(propylene oxide) is reduced. In the Example of GB-A-2348200, a ceramic ultrafiltration membrane having a pore size of 6 nm was used in separating poly(propylene oxide) from propylene oxide. In said Example, it is stated that it was found that said membrane removed about 50% poly(propylene oxide). More in particular, it appears that in said Example, the poly(propylene oxide) concentration in the propylene oxide feed was 1.03 mg/l and that the poly(propylene oxide) concentration in the permeate was still 0.54 mg/l. This corresponds with a PPO rejection of only 48%.

In the above-discussed prior art methods for removing poly(propylene oxide) from propylene oxide by membrane separation, ultrafiltration membranes are used. Ultrafiltration is a pressure difference driven membrane filtration technique, wherein porous membranes are used which have an average pore size greater than 5 nm. One of the disadvantages of using ultrafiltration membranes as discussed above, is that the membranes foul during operation (membrane pores getting clogged or plugged) and have eventually to be taken out of operation for cleaning purposes. This will severely decrease the separation efficiency in time. A further disadvantage of using polymeric ultrafiltration membranes, is that they swell. Swelling has an effect on the pore size and results in permeability and selectivity instability.

In summary, from the above discussion of prior art methods for removing poly(propylene oxide) from propylene oxide by membrane separation, it appears that there is still a need in the art for a process using a membrane which, during a relatively long period of time, can separate poly(propylene oxide) from propylene oxide, in a stable way, both in terms of a stable PPO rejection and in terms of a stable permeate flow. In addition, this constant, stable PPO rejection should be sufficiently high such that the permeate produced at any time, can be used for example in the production of moulded polyurethane foams and/or slabstock polyurethane foams.

SUMMARY OF THE INVENTION

It is the object of the present invention to fulfil said need and to provide a process for removing poly(propylene oxide) from propylene oxide by membrane separation, which does not have the disadvantages of the prior art processes as discussed above. This object is achieved by using a membrane which is a non-porous (no pores) or nanofiltration (pores having an average size of at most 5 nm) membrane. As further discussed below, such non-porous and nanofiltration membranes are commonly referred to in the art as dense membranes and work in a similar way. Accordingly, the process according to the present invention is a process for removing poly(propylene oxide) from propylene oxide by membrane separation, wherein a membrane having an average pore size of from 0 to 5 nm is used.

DETAILED DESCRIPTION OF THE INVENTION

Preferably, the membrane to be used in the present invention is resistant to hydrocarbons, such as propylene oxide. This implies that the membrane does not dissolve in the propylene oxide which it has to purify.

In general, in a process for removing poly(propylene oxide) from propylene oxide by membrane separation, a liquid feed comprising propylene oxide and poly(propylene oxide) is separated by the membrane into a permeate comprising propylene oxide and either no poly(propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

Applicants have found that when using a non-porous or nanofiltration membrane, very good and stable separation results are obtained in such process for removing poly(propylene oxide) from propylene oxide. For example, less fouling of the membrane occurs and therefore the membrane has to be taken out of operation less frequently than when using an ultrafiltration membrane as in the above-discussed prior art processes. Therefore, the present process can be performed efficiently on a continuous basis.

The use of a non-porous or nanofiltration membrane in purifying hydrocarbons in general, is described in WO-A-01060771 (which is in the name of Shell). This document discloses a process for purifying a liquid hydrocarbon product comprising 5% by weight or less of high molecular weight contaminants having a molecular weight of at least 1000, wherein the product stream is contacted with a non-porous or nanofiltration membrane and the purified product stream is recovered as the permeate. Although there is no specific limitation as to the nature of the liquid hydrocarbon product in WO-A-01060771, the products specifically mentioned are typically industrially produced chemical product streams containing a polymerisable olefinic bond. The products may include one or more heteroatoms, and named examples of liquid hydrocarbon products include hydrocarbon per se, such as cyclopentadiene, dicyclopentadiene, 1,3-cyclohexadiene, cyclohexene, styrene, isoprene, butadiene, cis-1,3-pentadiene, trans-1,3-pentadiene, benzene, toluene, xylenes, ethene and propene. Named liquid hydrocarbon products containing heteroatoms are methyl acrylate, ethyl acrylate and methylmethacrylate. However, there is no mention in WO-A-01060771 of purification of a propylene oxide stream comprising poly(propylene oxide) by means of a non-porous or nanofiltration membrane.

The non-porous or nanofiltration membrane to be used in the present invention may be of the ceramic or polymeric type. Preferably, the membrane used is hydrophobic because the stream to be treated is a hydrocarbon stream which should be capable of passing through the membrane. An additional advantage of using a hydrophobic membrane rather than a hydrophilic one, is that using a hydrophobic membrane will prevent water from passing the membrane and entering the permeate. It is well known that water may initiate polymerisation of propylene oxide, resulting in a polyol, which is undesired.

Non-porous and nanofiltration membranes are commonly referred to in the art as dense membranes. Examples of non-porous and nanofiltration membranes are reverse osmosis type membranes. Non-porous and nanofiltration membranes should be distinguished from ultrafiltration membranes which are always porous. Ultrafiltration membranes have an average pore size of greater than 5 nm up to about 800 nm. Where nanofiltration membranes are used which are porous, they have an average membrane pore size which is at most 5 nm (nanoporous membranes). Where such nanofiltration or nanoporous membrane is used in accordance with the present invention, the average membrane pore size is suitably less than 5 nm, preferably at most 3 nm, more preferably at most 2 nm, more preferably at most 1 nm, more preferably at most 0.7 nm, more preferably at most 0.5 nm, more preferably at most 0.3 nm, more preferably at most 0.1 nm, more preferably at most 0.05 nm, and most preferably at most 0.01 nm.

The term "poly(propylene oxide)" as used throughout the present specification in relation to the present invention, refers to poly(propylene oxide) having a molecular weight of 1500 Dalton or higher, or having a molecular weight of 1000 Dalton or higher, or having a molecular weight of 900 Dalton or higher, or having a molecular weight of 750 Dalton or higher, or having a molecular weight of 500 Dalton or higher, unless stated otherwise. The molecular weights as used throughout this specification are expressed in Dalton (1 Da=1 g/mole) and are based on a determination by size-exclusion chromatography (SEC) as is further explained in the present Examples.

Non-porous and nanofiltration membranes as such are known in the art and in principle any non-porous or nanoporous membrane capable of retaining 80% by weight or more, preferably 90% by weight or more, most preferably 95% by weight or more, and very highly preferably 99% by weight or more of the poly(propylene oxide), can be used in the present invention. The upper limit for the molecular weight of the poly(propylene oxide) to be removed, is not critical and may be as high as 500,000.

In a preferred embodiment of the present invention, the non-porous or nanofiltration membrane is a polymeric membrane. Such polymeric membrane is preferably cross-linked to provide the necessary network for avoiding dissolution of the membrane once being in contact with propylene oxide. In general, cross-linking can be effected in several ways, for instance by reaction with cross-linking agents (chemical cross-linking) and/or by irradiation. Preferably, the membrane layer has a siloxane structure which has been cross-linked by means of irradiation, as is for example described in WO-A-9627430.

Examples of suitable, presently available cross-linked non-porous or nanofiltration membranes are cross-linked silicone rubber-based membranes, of which the cross-linked polysiloxane membranes are a particularly useful group of membranes. Such cross-linked polysiloxane membranes are known in the art, for example from U.S. Pat. No. 5,102,551.

Typically, the polysiloxanes used contain the repeating unit —Si—O—, wherein the silicon atoms bear hydrogen or a hydrocarbon group. Preferably the repeating units are of the formula (I)

$$-\text{Si}(R)(R')-O- \quad (I)$$

wherein R and R' may be the same or different and represent hydrogen or a hydrocarbon group selected from the group consisting of alkyl, aralkyl, cycloalkyl, aryl, and alkaryl. Preferably, at least one of the groups R and R' is an alkyl group, and most preferably both groups are alkyl groups, more especially methyl groups. The alkyl group may also be a 3,3,3-trifluoropropyl group. Very suitable polysiloxanes for the purpose of the present invention are (—OH or —NH$_2$ terminated) polydimethylsiloxanes and polyoctylmethylsiloxanes. Thus, preferably, the polysiloxane is cross-linked. The cross-linking may be effected through a reactive terminal —OH or —NH$_2$ group of the polysiloxane. Preferred polysiloxane membranes are cross-linked elastomeric polysiloxane membranes.

Examples of suitable cross-linked elastomeric polysiloxane membranes are extensively described in above-mentioned U.S. Pat. No. 5,102,551. Thus, suitable membranes are composed of a polysiloxane polymer such as described supra having a molecular weight of 550 to 150,000, preferably 550 to 4200 (prior to cross-linking), which is cross-linked with, as cross-linking agent, (i) a polyisocyanate, or (ii) a poly(carbonyl chloride) or (iii) R$_{4-a}$Si(A)$_a$ wherein A is —OH, —NH$_2$, —OR, or —OOCCR, a is 2, 3, or 4, and R is hydrogen, alkyl, aryl, cycloalkyl, alkaryl, or aralkyl. Further details regarding suitable polysiloxane membranes can be found in U.S. Pat. No. 5,102,551.

For the purpose of the present invention the preferred non-porous membrane is a polydimethylsiloxane membrane, which is preferably cross-linked. Also other rubbery non-porous membranes could be used. In general, rubbery membranes can be defined as membranes having a non-porous top layer of one polymer or a combination of polymers, of which at least one polymer has a glass transition temperature well below the operating temperature, i.e. the temperature at which the actual separation takes place. Yet another group of potentially suitable non-porous membranes are the so called superglassy polymers. An example of such a material is poly(trimethylsilylpropyne).

The non-porous or nanofiltration membrane is typically supported on at least one porous substrate layer to provide the necessary mechanical strength. Suitably, this other porous substrate layer is made of a porous material of which the pores have an average size greater than 5 nm. Such other porous material may be a microporous, mesoporous or macroporous material which is normally used for microfiltration or ultrafiltration, such as poly(acrylonitrile). The thickness of the base layer should be sufficiently to provide the necessary mechanical strength. In addition, this substrate may in return be supported on a further porous support to provide the required mechanical strength. Typically, the thickness of the base layer is of from 100 to 250 μm, more suitably of from 20 to 150 μm. Where the non-porous or nanofiltration membrane is combined with such base layer, the membrane suitably has a thickness of from 0.5 to 10 μm, preferably of from 1 to 5 μm.

The combination of a thin top membrane layer and a thick porous support layer is often referred to as composite membranes or thin film composites. The membrane is suitably so arranged that the permeate flows first through the membrane top layer and then through the base layer, so that the pressure difference over the membrane pushes the top layer onto the base layer. Suitable porous materials for the base layer having an average pore size greater than 5 nm, are poly(acrylonitrile), poly(amideimide)+$TiO_2$, poly(etherimide), polyvinylidenedifluoride and poly(tetrafluoroethylene). Poly(acrylonitrile) is especially preferred. The preferred combination according to the present invention is a poly(dimethylsiloxane)-poly(acrylonitrile) combination.

The non-porous or nanofiltration membrane may also be used without a substrate layer, but it will be understood that in such a case the thickness of the membrane should be sufficient to withstand the pressures applied. A thickness greater than 10 μm may then be required. This is not preferred from a process economics viewpoint, as such thick membrane will significantly limit the throughput of the membrane, thereby decreasing the amount of purified product which can be recovered per unit of time and membrane area.

When using a non-porous or dense membrane, transmission of the permeate takes place via the solution-diffusion mechanism. The propylene oxide to be permeated dissolves in the membrane matrix and diffuses through the thin selective membrane layer, after which it desorbs at the permeate side. The main driving force for permeation is hydrostatic pressure. Examples of such membranes are reverse osmosis type membranes. In case a nanoporous membrane is used in the present invention, it is believed that separation takes place both on the basis of the above-mentioned solution-diffusion mechanism and on the basis of molecular size differences. In the latter case, there is no question of dissolution of the permeate in the membrane matrix but only of transport through the membrane via its nanopores. Where such solution-diffusion mechanism is functioning, it is believed to be important that the membrane material does not dissolve the contaminant to be removed from the membrane feed but, preferentially, only the component that has to be freed from the contaminant. The present inventors have found that especially polysiloxane membranes, for example poly(dimethylsiloxane) membranes, are capable of such preferential dissolution of propylene oxide, rather than poly(propylene oxide) which they do not dissolve.

An advantage of using non-porous membranes as compared to the use of nanoporous membranes is that there is no plugging effect. This means that there is no possibility of the membrane becoming blocked by larger molecules plugged in the pores. This could happen in porous membranes, as a result of which it is more difficult to regenerate a stable flux. Therefore, it is preferred for the purpose of the present invention to use a non-porous or dense membrane. However, it is emphasised that nanoporous membranes could also be used in the process of the present invention as a nanofiltration membrane.

The retentate will still comprise valuable propylene oxide and for that reason the retentate may suitably be recycled to the membrane separation step and mixed with fresh feedstock. However, when recycling retentate, part of the retentate will have to be discharged such as to avoid build up of the poly(propylene oxide) which is to separated from the propylene oxide by means of said membrane process. Instead of recycling the retentate within the same process, it may also be subjected to a second and optionally further separation step, in which case the retentate of a first separation step is used as the feed for a second separation step.

Further, instead of recycling (part of) the retentate or further purifying it in a second and optionally further step, the retentate may also be discharged in its entirety. This is most likely advantageous where the composition of the retentate is such that it has some value as a starting material in another process, without having to further treat the retentate before such use (no further processing). The permeate has been upgraded in the sense that its contamination level has been lowered. Consequently the permeate has obtained a higher value compared to the original product. The retentate, which contains an increased proportion of poly(propylene oxide) as compared to the original product, has a value depending on the poly(propylene oxide) concentration and the perceived end use. The retentate value may be lower than or similar to the value of the original feed.

Stage cut is defined as the weight percentage of the original feed that passes through the membrane and is recovered as permeate. By adjusting the stage cut, it is possible to vary the concentration of a contaminant in the permeate, as well as the concentration of said same contaminant in the retentate. The higher the stage cut, the higher the contaminant concentration in the retentate.

In the present invention, the stage cut can vary within broad limits: 10 to 99% by weight, suitably 30 to 95% by weight or 50 to 90% by weight. All that matters is that a poly(propylene oxide) concentration in permeate and/or retentate is achieved which is below a certain maximum. For example, where it is intended to use the permeate in the production of moulded polyurethane foam, a relatively high stage cut might have to be achieved. Another relevant factor to consider is the poly (propylene oxide) concentration in the feed.

The desired stage cut can be set by varying, for a given permeability of the membrane, the trans-membrane pressure and/or the feed flow. The first option implies that, for a given feed flow, increasing the trans-membrane pressure results in a greater flux or flow of the permeate through the membrane, and therefore in a higher stage cut. According to the second option, such higher stage cut may also be achieved by decreasing the feed flow whilst maintaining a certain permeate flow through the membrane.

In the present invention, the volume flux through the membrane is typically in the range of from 5 to 1000, suitably 10 to 500, and more suitably 15 to 200 $l/h/m^2$. The flux through the membrane may also be expressed as mass flux. Preferably, the flux through the membrane is constant in time. Further, the inlet stream is contacted with the membrane at a trans-membrane pressure (pressure difference) which is typically in the range of from 1 to 60 bar, suitably 3 to 35 bar, and more suitably 3 to 25 bar. The permeability of the membrane is typically in the range of from 1 to 100, suitably 2 to 50, and more suitably 3 to 10 $l/h/m^2/bar$.

In accordance with the present invention, a liquid feed comprising propylene oxide and poly(propylene oxide) may be separated by a non-porous or nanofiltration membrane into a permeate comprising propylene oxide and either no poly (propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

Preferably, the poly(propylene oxide) concentration in said permeate is from essentially zero to at most 10 ppmw (parts per million by weight), more preferably at most 5 ppmw, more preferably at most 3 ppmw, more preferably at most 1 ppmw, more preferably at most 0.5 ppmw, more preferably at most 0.3 ppmw, and most preferably at most 0.1 ppmw, on the basis of total weight of the permeate. Such permeate may suitably be used as raw material in making a polyether polyol to be used in making slabstock polyurethane foam.

Further, preferably, the poly(propylene oxide) concentration in said permeate is from essentially zero to less than 1 ppmw, more preferably from essentially zero to 0.5 ppmw, more preferably from essentially zero to 0.3 ppmw, and most preferably from essentially zero to 0.1 ppmw, on the basis of total weight of the permeate. Such permeate may suitably be used as raw material in making a polyether polyol to be used in making either slabstock polyurethane foam or moulded polyurethane foam.

In particular, where propylene oxide is to be used in making moulded polyurethane foam, the concentration of poly(propylene oxide) having a molecular weight of 20,000 and higher, in such propylene oxide, should preferably not exceed 0.5 ppmw. More preferably, the concentration of said higher molecular weight poly(propylene oxide) is at most 0.4 ppmw.

Preferably, the poly(propylene oxide) concentration in said retentate is from essentially zero to at most 20 ppmw, more preferably at most 10 ppmw, more preferably at most 5 ppmw, more preferably at most 3 ppmw, and most preferably at most 2 ppmw, on the basis of total weight of the retentate. Such retentate may suitably be used as raw material in making a polyether polyol to be used in making slabstock polyurethane foam.

Thus, a further advantage is that in addition to the permeate, the retentate can also have some end use value as long as the stage cut is properly controlled.

The membrane separation will be performed in a membrane unit, which comprises one or more membrane modules. Examples of suitable modules are typically expressed in how the membrane is positioned in such a module. Examples of these modules are the spirally wound, plate and frame (flat sheet), hollow fibres and tubular modules. Preferred module configurations are spirally wound and plate and frame. Most preferably, the non-porous or nanofiltration membrane is applied in a membrane unit, which comprises spirally wound membrane modules. These membrane modules are well known to the skilled person as for example described in Encyclopedia of Chemical Engineering, 4$^{th}$ Ed., 1995, John Wiley & Sons Inc., Vol 16, pages 158-164. Examples of spirally wound modules are described in for example, U.S. Pat. No. 5,102,551, U.S. Pat. No. 5,093,002, U.S. Pat. No. 5,275,726, U.S. Pat. No. 5,458,774, U.S. Pat. No. 5,150,118, and WO-A-2006040307.

It will be appreciated that preferably the operating temperature should be kept below the boiling point of the propylene oxide feed in order to have a liquid inlet stream. The boiling point of propylene oxide is about 34° C. Thus, at atmospheric pressure temperatures from 0° C. up to 34° C. may be applied. Suitably, the separation is carried out at a temperature in the range of from 5 to 30° C., more suitably at ambient temperature.

The way in which the propylene oxide to be purified in accordance with the present invention is prepared, is immaterial to the present invention. Any known preparation process may have been applied. The propylene oxide to be treated in the process according to the present invention may be the product directly obtained from the known preparation processes. Alternatively, said directly obtained propylene oxide also may have been subjected to conventional purification and recovery techniques before it is treated in accordance with the present invention. Assuming that the propylene oxide is produced in a hydroperoxide process, such purification and recovery techniques typically involve the removal of unreacted propene and organic hydroperoxide, by-products (like propane, aldehydes and alcohol) and other treating agents. Typically, the propylene oxide feed to be purified in the present process, has been obtained by the epoxidation of propene using ethylbenzene hydroperoxide as the oxidant, then separating propene from the product mixture comprising propylene oxide and methyl phenyl carbinol, and finally separating propylene oxide from the methyl phenyl carbinol.

In general, the propylene oxide stream to be treated in the process of the present invention comprises at least 95 wt % of propylene oxide.

If the propylene oxide product to be treated is a relatively crude propylene oxide stream, such product may contain 5% by weight or less of poly(propylene oxide) based on total weight of the product. However, the present method is particularly suitable when the propylene oxide product to be treated contains 3% by weight or less, suitably 1% by weight or less, and more suitably 0.1% by weight or less of the poly(propylene oxide). Even at such relatively high poly(propylene oxide) levels, the process of the present invention is highly effective.

If the propylene oxide product to be treated is a relatively pure propylene oxide stream, such product preferably contains less than 500 ppmw, suitably less than 300 ppmw, more suitably less than 200 ppmw, more suitably less than 100 ppmw, more suitably less than 50 ppmw, and most suitably less than 20 ppmw of poly(propylene oxide). Typically, such relatively pure propylene oxide inlet stream comprises 1 to 15 ppmw of poly(propylene oxide).

The invention is further illustrated by the following Examples.

EXAMPLE 1 AND COMPARATIVE EXAMPLES 1 AND 2

Poly(propylene oxide) (PPO) was removed from a propylene oxide (PO) feed by using a dead-end membrane unit. In a dead-end membrane unit, the feed flows perpendicular to the membrane surface. The experimental set-up used in these examples is schematically shown in FIG. 1, wherein the reference numerals have the following meanings:

| | |
|---|---|
| 1: | stirrer |
| 2: | nitrogen inlet |
| 3: | PO/PPO feed mixture |
| 4: | membrane |
| 5: | permeate outlet |
| 6: | collection vessel |

In these examples, the pressure difference over membrane 4 of the dead-end membrane unit of FIG. 1, necessary for effecting the flow of permeate through the membrane, was applied by means of pressurisation by feeding nitrogen gas via nitrogen inlet 2. In addition, the nitrogen was used as a blanket covering PO/PPO feed mixture 3. The trans-membrane pressure applied was 5 bar during the entire experimental period.

After having applied said trans-membrane pressure, the vessel shown in FIG. 1 was filled with 140 grams of the PO/PPO feed. Subsequently, stirring of this feed under a blanket of nitrogen gas was started by using stirrer 1. Said stirring was carried out during a time period of 75 minutes at which time about 70 grams of the original feed had permeated through the membrane. The stage cut was therefore about 50 wt. %. The temperature during the entire experimental period was room temperature.

In Example 1, a supported membrane was used wherein the top layer having a thickness of approximately 3 μm was made of hydrophobic non-porous (dense) cross-linked poly(dimethylsiloxane) (PDMS). The total membrane surface was 5 cm$^2$.

In Comparative Examples 1 and 2, different types of membranes were used, namely ultrafiltration porous membranes having a pore size greater than 5 nm and being made of either poly(acrylonitrile) (PAN) or poly(vinylidene fluoride) (PVDF), as disclosed in U.S. Pat. No. 5,248,794 which is discussed in the introduction of this specification.

In Comparative Example 1, a supported membrane was used wherein the top layer having a thickness of approximately 3 μm was made of hydrophobic porous poly(acrylonitrile) (PAN) having an average pore size of 25 nm. The total membrane surface was 5 cm².

In Comparative Example 2, a supported membrane was used wherein the top layer having a thickness of approximately 3 μm was made of hydrophobic porous poly(vinylidene fluoride) (PVDF) having an average pore size of 20 nm. The total membrane surface was 5 cm².

At the end of the above-mentioned time period, the part of the PO/PPO feed mixture which remained inside the vessel and which did not pass through the membrane as the permeate, was decanted and recovered as the retentate. The PPO concentrations in the retentate and the permeate were determined. These PPO concentrations are shown in Table 1, as well as the PPO concentration of the feed at the beginning of the experiment.

The PPO concentrations were determined by means of combined size-exclusion chromatography (SEC) and refractive index detection. A test sample of propylene oxide is evaporated and the residue thus obtained is dissolved in tetrahydrofuran (THF). An aliquot of the solution thus obtained is injected onto a SEC column. The molecules are separated according to their hydrodynamic volume (so-called size) in solution. The separated molecules are detected by a high sensitivity differential refractive index (dRI) detector and recorded as they elute from the column according to concentration. From the molecular weight distribution of the residue thus obtained, the fraction of high molecular weight PPO is identified using a polystyrene standard (PS) having an average molecular weight of 20,000 Da. For the quantification of this fraction, a poly(propylene glycol) (PPG) standard having an average molecular weight of 5,000 Da is applied, using a multi-point external standard calibration technique. The concentration (in mg/l) of the high molecular weight PPO (PS 20,000 Da and higher) in the sample was calculated by means of the following equation:

$$C_{cal} * V_{THF} / V_{PO}$$

where:

$C_{cal}$=concentration of the high molecular weight PPO in test solution as obtained from the calibration graph (in mg/l);

$V_{THF}$=total volume of THF added for dilution of residue; and $V_{PO}$=total volume of PO evaporated from test sample.

TABLE 1

|  | Ex. 1 | Comp. Ex. 1 | Comp. Ex. 2 |
|---|---|---|---|
| PPO concentration in feed (ppmw) | 273 | 273 | 273 |
| PPO concentration in permeate (ppmw) | <1 | 22 | 61 |
| PPO rejection (%) | >99 | 92 | 78 |
| PPO concentration in retentate (ppmw) | 746 | 493 | 409 |

From Table 1 it can be seen that the PPO rejection in Example 1 is higher than in Comparative Examples 1 and 2. The permeate obtained in Example 1, having a concentration of PPO having a molecular weight of 20,000 and higher, of less than 1 ppmw, may suitably be used as raw material in making a polyether polyol to be used in making moulded or slabstock polyurethane foam.

Still further, it was found that after having decanted the retentate, the membrane used in Example 1 could be used again to treat another PO/PPO batch at a similar flux resulting in a similar PPO rejection as in said Example 1. This implies that after use, the separation quality of the membrane used in Example 1 remains the same.

EXAMPLES 2 AND 3

A spiral wound membrane module similar to the one as shown in FIG. 1 of WO-A-2006040307 and as further described therein, was used, with the proviso that the module was made PO resistant, inter alia by using PO resistant spacers and seals, and that the membrane used was the same as the membrane used in Example 1 of the present specification. For a more detailed description of said module and the operation of it, reference is made to WO-A-2006040307.

In using a spiral wound membrane module, the feed flows parallel to the membrane surface with the inlet feed stream entering the membrane module at a certain composition (cross-flow operation). The feed composition inside the module changes as a function of distance in the module, while the feed stream is separated into two: a permeate stream and a retentate stream.

In the present Examples 2 and 3, the PPO concentration in both the permeate stream and the retentate stream were monitored. These concentrations were determined in the same way as in Example 1 and Comparative Examples 1 and 2 and are shown in Table 2, as well as the PPO concentration of the feed. During the entire experimental period, the trans-membrane pressure was 5 bar and the temperature was room temperature. The total membrane surface of the membrane used in Examples 2 and 3 was 1 m².

TABLE 2

|  | Ex. 2 | Ex. 3 |
|---|---|---|
| PPO concentration in feed (ppmw) | 116 | 4.9 |
| PPO concentration in permeate (ppmw) | 2.8 | 0.06 |
| PPO rejection (%) | 98 | 99 |
| PPO concentration in retentate (ppmw) | 153 | 6.4 |

Each of the experiments from Examples 2 and 3 was performed continuously during seven days. The permeability, flux, permeate flow velocity and retentate flow velocity were stable during that entire experimental period. In addition, the PPO rejection was stable.

From Table 2 it can be seen that the PPO rejection in Examples 2 and 3 is relatively high, almost 100%. This implies that the permeates obtained might be used as raw material in making a polyether polyol to be used in making moulded polyurethane foam. Indeed, the permeate obtained in Example 3 may suitably be used in the production of moulded polyurethane foam. Said permeate only contained 0.06 ppmw of PPO having a molecular weight of 20,000 and higher. However, the permeate obtained in Example 2 which originated from a more contaminated PO feed, is not suitable for use in the production of moulded polyurethane foam as it still contains too much PPO, more in particular 2.8 ppmw of PPO having a molecular weight of 20,000 and higher. This is far above 0.4 ppmw which in general is considered as the maximum allowable concentration of PPO having a molecular weight of 20,000 and higher, in PO to be used in the production of moulded polyurethane foam.

In addition to achieving a high PPO rejection during the entire experimental period, another advantage of the membrane used in the above spiral wound membrane module is that the permeability and flux remain at the same level during the entire experimental period. There was no question of plugging or clogging of said membrane.

What is claimed is:

1. A process for removing poly(propylene oxide) from a propylene oxide by membrane separation, wherein a membrane having an average pore size of from 0 to 5 nm is used, which membrane is a polymeric membrane made from a polysiloxane which contains repeating units of the formula (I)

$$—Si(R)(R')—O— \quad (I)$$

wherein R and R' may be the same of different and represent hydrogen or a hydrocarbon group selected from the group consisting of alkyl, aralkyl, cycloalkyl, aryl, and alkaryl.

2. A process according to claim 1, wherein a liquid feed comprising propylene oxide and poly(propylene oxide) is separated by the membrane into a permeate comprising propylene oxide and either no poly(propylene oxide) or poly(propylene oxide) at a concentration which is lower than the poly(propylene oxide) concentration in the feed, and a retentate comprising propylene oxide and poly(propylene oxide) at a concentration which is higher than the poly(propylene oxide) concentration in the feed.

3. A process according to claim 2, wherein the poly(propylene oxide) concentration in the permeate is from zero to at most 3 ppmw, on the basis of total weight of the permeate.

4. A process according to claim 2, wherein the poly(propylene oxide) concentration in the permeate is from zero to less than 1 ppmw, on the basis of total weight of the permeate.

5. A process according to claim 3, wherein the permeate is for use as raw material in making a polyether polyol to be used in making slabstock polyurethane foam.

6. A process according to claim 4, wherein the permeate is for use as raw material in making a polyether polyol to be used in making moulded polyurethane foam.

7. A process according to claim 2, wherein the poly(propylene oxide) concentration in the retentate is from zero to at most 3 ppmw, on the basis of total weight of the retentate.

8. A process according to claim 7, wherein the retentate is for use as raw material in making a polyether polyol to be used in making slabstock polyurethane foam.

9. A process according to claim 1, wherein the separation is carried out at a temperature in the range of from 5 to 30° C.

10. A process according to claim 4, wherein the permeate is for use as raw material in making a polyether polyol to be used in making slabstock polyurethane foam.

* * * * *